United States Patent
Bakhtyari-Nejad-Esfahani

(10) Patent No.: US 8,323,186 B2
(45) Date of Patent: Dec. 4, 2012

(54) DEVICE FOR FACILITATING THE MEDICAL EXAMINATION OF AN ORIFICE

(75) Inventor: Arash Bakhtyari-Nejad-Esfahani, Nottinghamshire (GB)

(73) Assignee: Olberon Limited, Nottingham (GB)

( * ) Notice: Subject to any disclaimer, the term of this patent is extended or adjusted under 35 U.S.C. 154(b) by 471 days.

(21) Appl. No.: 12/295,266

(22) PCT Filed: Mar. 29, 2007

(86) PCT No.: PCT/GB2007/050170
§ 371 (c)(1),
(2), (4) Date: Sep. 29, 2008

(87) PCT Pub. No.: WO2007/110674
PCT Pub. Date: Oct. 4, 2007

(65) Prior Publication Data
US 2009/0171162 A1    Jul. 2, 2009

(30) Foreign Application Priority Data
Mar. 29, 2006   (GB) .................................. 0606286.3

(51) Int. Cl.
*A61B 1/32* (2006.01)

(52) U.S. Cl. ........................................ 600/235; 600/246

(58) Field of Classification Search ................. 600/201, 600/213, 220, 221, 223, 226, 227, 245, 235, 600/246
See application file for complete search history.

(56) References Cited

U.S. PATENT DOCUMENTS

| | | | |
|---|---|---|---|
| 4,299,219 A | 11/1981 | Norris, Jr. | |
| 4,332,248 A | 6/1982 | DeVitis | |
| 4,337,763 A * | 7/1982 | Petrassevich | 600/210 |
| 4,393,870 A | 7/1983 | Wagner | |
| 4,576,168 A | 3/1986 | Jalowayski | |
| 4,586,924 A | 5/1986 | Lanning | |
| 4,619,248 A | 10/1986 | Walsh | |
| 4,638,792 A | 1/1987 | Burgin | |
| 4,664,651 A | 5/1987 | Weinshenker | |
| 5,320,607 A | 6/1994 | Ishibashi | |
| 5,415,647 A | 5/1995 | Pisarik | |
| 5,984,890 A | 11/1999 | Gast et al. | |
| 6,669,703 B2 * | 12/2003 | Shue | 606/119 |
| 6,814,737 B2 * | 11/2004 | Cauthen | 606/99 |
| 2004/0023184 A1 * | 2/2004 | de Josselin de Jong et al. | 433/30 |

FOREIGN PATENT DOCUMENTS

| | | |
|---|---|---|
| DE | 824662 | 12/1951 |
| DE | 8712654 | 10/1988 |
| DE | 19620314 A1 | 11/1997 |
| FR | 2612401 A | 9/1988 |
| FR | 2698778 A1 | 6/1994 |
| GB | 0553728 A | 3/1946 |
| RU | 2109525 C1 | 4/1998 |
| WO | WO9825512 A1 | 6/1998 |
| WO | WO01/34019 A | 5/2001 |
| WO | WO02100457 A | 12/2002 |

* cited by examiner

*Primary Examiner* — Cris L Rodriguez
*Assistant Examiner* — Eric Rosen
(74) *Attorney, Agent, or Firm* — Knobbe Martens Olson & Bear LLP

(57) ABSTRACT

A device for facilitating the examination of an orifice includes a mount for a light source for illuminating the orifice, a connector for detachably mounting a dilator for insertion into and dilation of an orifice, and an actuator for operating a mounted dilator. The mounted dilator includes operative parts able to move apart from one another.

34 Claims, 8 Drawing Sheets

DEVICE FOR FACILITATING THE MEDICAL EXAMINATION OF AN ORIFICE

CROSS REFERENCE TO RELATED APPLICATIONS

This application claims the benefit and priority to and is a U.S. National Phase of PCT International Application Number PCT/GB2007/050170, filed on Mar. 29, 2007. This application claims the benefit and priority to United Kingdom Application No. GB 0606286.3 filed on Mar. 29, 2006. The disclosures of the above-referenced applications are hereby expressly incorporated by reference in their entirety.

The present invention relates to a device for facilitating the examination of an orifice, and in particular to a device for use in examining a nostril and/or an ear.

Currently, ear, nose and throat specialists examine a patient's nose using a handheld speculum to dilate each nostril. A head mirror is used to direct light from an external source into the patient's nostril while it is being examined. This complex arrangement is difficult for a non-specialist to master. Routine examination of the nose by a non-specialist is thus difficult and sometimes inadequate. Moreover, a metal speculum is used for each patient, and must be sterilized before it can be reused.

Non-specialists often use a handheld otoscope to examine the nose. An otoscope is a device designed for examining the ear. Use of an otoscope to examine the nose is problematic for several reasons. An otoscope has an integral lens which can quickly mist up so that the doctor's view is obstructed. Moreover, the aperture of an otoscope is fixed; it therefore does not allow dilation of the nostril. Finally, an otoscope does not allow procedures such as the administration of drugs into the nose to take place.

Rhinoscopes including an integrated light source and speculum are known. However, as these include an integrated speculum, cleaning and sterilization of the device between patients is necessary. Inadequate cleaning of these devices may lead to the transfer of infection from one patient to another.

According to a first aspect of the present invention there is provided a device for facilitating the examination of an orifice, the device comprising mounting means for a light source for illuminating the orifice, a connector for detachably mounting a dilator for insertion into and dilation of an orifice, and dilator actuating means for operating a mounted dilator, the mounted dilator including operative parts able to move apart from one another.

This arrangement provides a device that is able both to illuminate and to dilate an orifice. All of the elements needed by an ear, nose and throat specialist (a light directed into the nostril and a dilator, also referred to as a speculum) have therefore been integrated into a single handheld device that can be used easily and effectively by non-specialists. Moreover, because the dilator is detachably mounted to the device, it can be easily removed and cleaned, or replaced, between different patients. This enables multiple successive patients to be examined quickly, without risk of cross-infection.

Inclusion of dilator actuating means within the device, rather than the dilator, means that dilators for use with the device can be of simple construction, and therefore cheap to manufacture and preferably disposable. Furthermore, the dilator actuating means is preferably adapted to engage parts of the dilator that are remote from those parts of the dilator that are engaged with the connector of the device. In this way, the connector may be adapted to fasten parts of the dilator to the device in a fixed position relative to a casing of the device, and hence the dilator and connector of the device may be of simple construction.

The dilator actuating means preferably comprises an actuating member adapted to urge adjacent parts of the dilator apart, thereby causing the operative parts to move apart from one another and hence dilate the orifice. The actuating member preferably includes an actuating projection for insertion between adjacent parts of a mounted dilator, such that movement of the actuating projection relative to the dilator causes the operative parts of the dilator to move apart from one another. The actuating member is preferably movable by a user, either directly or by means of an operably connected engagement member, to actuate the dilator.

The actuating member is preferably resiliently biased to an inoperative configuration, in which the dilator is in a contracted configuration. This resilient biasing of the actuating member facilitates accurate control of the movement of the actuating member, and thus facilitates accurate control of the dilation of the orifice by the dilator. The device preferably therefore includes one or more resilient members, such as one or more springs, that act upon the actuating member. A smoother movement of the actuating member may be achieved using a plurality of springs, rather than a single spring.

The actuating member or associated engagement member is preferably adapted to be moved by the thumb or a finger of the user, and preferably includes a platform with an operative surface upon which a user's thumb or finger may rest. Most preferably, the actuating member is arranged such that pressure applied by a user's thumb or finger to the operative surface causes movement of the actuating member. The platform preferably extends about a casing of the device to a sufficient extent that the actuating member is operable by the left or right hand of a user, during normal use.

In presently preferred embodiments, the actuating member is slidably mounted to the exterior of a casing of the device, and most preferably has the form of a ring mounted about the casing. In this case, the actuating member is preferably engaged with one or more slots in the casing that enable slidable movement of the actuating member relative to the casing. The one or more slots in the casing with which the actuating member is engaged are preferably adapted to reduce the risk that the actuating member is accidentally disengaged from the casing by the biasing of the resilient means. Most preferably, the one or more slots include a dogleg formation.

The device is preferably suitable for facilitating examination of a nostril, and hence is a rhinoscope. Most preferably, however, the device is also suitable for facilitating examination of an ear, and hence is also an otoscope. In particular, the device preferably includes a magnifying lens that is able to provide an enlarged view of the interior of an ear. In order for the device to be suitable for use examining a nostril and an ear, the magnifying lens is preferably movably mounted to the device. Most preferably, the lens is movable between an operative position in which it is able to provide an enlarged view of the interior of the orifice, and an inoperative position in which the view of the orifice, in use, through the dilator is unobstructed by the lens. In presently preferred embodiments, the lens is mounted to a rotatable arm, such that rotation of the arm causes the lens to be moved between operative and inoperative positions. Most preferably, the arm is mounted to an upper surface of the device, the arm being rotatable about an axis that is laterally offset from the lines of sight through the dilator, and is orientated generally perpendicularly to the upper surface of the device. Alternatively, the lens could be slidably mounted to an exterior surface of the device, so as to be movable between operative and inoperative positions. In this case, it may be necessary to adapt the actuating member to be engageable by a user on each side of the device, rather than at the rear where the lens is preferably slidably mounted.

The connector for detachably mounting the dilator preferably includes formations that engage with corresponding formations of the dilator, so as to fasten the dilator to the device. In particular, the connector may include one or more projections and/or depressions, and one or more corresponding depressions and/or projections could then be provided on an external surface of the dilator. Of course, any suitable arrangement of formations could be used. In presently preferred embodiments, the connector is adapted to receive part of the dilator with a close fit.

The mounting means for a light source is preferably a connector adapted for electrically connecting the device to a mounted light source. Most preferably, the source of power for the light source is a separate component that is connectable to the device. The device preferably therefore includes means for electrically connecting the device to a power source. In presently preferred embodiments, the power source is a battery unit adapted for connection to the device. The device preferably therefore includes a connector adapted for connection to a power source, such as a battery unit, and an electrical connection between the connected power source and the connected light source. The device most preferably includes a threaded connection that enables the device to be connected to existing battery units used for other diagnostic devices (for example a conventional otoscope or opthalmoscope).

The light source is preferably directed in the same direction as the transversely extending part of nasal speculum is orientated. This arrangement of the light source enables the doctor to maximise illumination of the orifice.

According to a further aspect of the present invention there is provided a dilator for use with the device for facilitating the examination of an orifice that is described above, the dilator comprising first and second speculum blades that each have a connection end adapted for detachable connection to the device, and an operative end adapted for insertion into an orifice, the operative ends being resiliently separable, in use, by the dilator actuating means of the device.

The speculum blades may be connectable together when removed from the device, or may be held together by the connector of the device. Preferably, the speculum blades each include a connector having connecting formations adapted to cooperate with corresponding formations of the connector of the device. Provision of connectors on the dilator ensures a reliable fit between the dilator and the device for facilitating the examination of an orifice.

In presently preferred embodiments, the dilator comprises two opposing speculum blades. The operative ends of the speculum blades are preferably adapted to enable the interior of the orifice to be viewed, in use, through the operative ends of the dilator. In particular, the operative ends of the speculum blades preferably together define a generally funnel-shaped member. However, the operative ends of the speculum blades preferably have a separation at all times, in use, in order to reduce the risk of trapping any hairs of the patient between the blades. Each speculum blade preferably also includes a body that extends between the operative end and the connection end. The bodies of the speculum blades are preferably sufficiently rigid that when adjacent parts of the bodies are urged apart, in use, the operative ends of the speculum blades are separated, and also sufficiently resilient that the bodies return to their original configurations when not actuated by the device. However, the bodies of the speculum blades are also preferably sufficiently flexible that the user is able to separate the bodies, in use, without excessive effort. The bodies may therefore include a weakened portion, situated below the adjacent parts of the bodies acted upon by the dilator actuating means, that reduces the force required to separate the operative ends of the speculum blades.

Preferably a groove having a gradually reducing width is provided between the two speculum blades, and preferably between the bodies of those blades, that enables an actuating projection to increase the separation of the operative ends of the speculum blades as the projection is moved along the groove. The groove preferably therefore reduces in width as it extends towards the connection ends of the speculum blades. An end of the groove adjacent to the operative ends of the blades is preferably able to accommodate at least part of the dilator actuating means, and most preferably the actuating projection, of the device when the dilator is in a contracted configuration. Subsequent movement of the actuating projection along the groove towards the connection ends of the speculum blades preferably causes a smooth and gradual separation of the operative ends of the speculum blades.

In presently preferred embodiments, the groove between the speculum blades includes two or more sections, and most preferably two sections, that reduce in width at different rates, and hence cause different rates of separation of the operative ends relative to movement of the actuating projection along the groove. In particular, the groove preferably includes a first section that causes separation of the operative ends at a first rate relative to movement of the actuating projection along the groove, and a second section that causes separation of the operative ends at a second rate relative to movement of the actuating projection along the groove, the second rate of separation being greater than the first rate. The first section is preferably formed at the end of the groove adjacent to the operative ends of the speculum blades, and the second section is preferably formed at the end of the groove adjacent to the connection ends of the speculum blades, so that the rate of change of small separations relative to movement of the actuating projection is less than the rate of change of large separations relative to movement of the actuating projection. Small separations of the operative ends caused by the first section of the groove are preferably suitable for dilation of an ear, and large separations of the operative ends caused by the second section of the groove are preferably suitable for dilation of a nose.

According to a further aspect of the present invention there is provided a kit including a device for facilitating examination of an orifice as described above, and at least one dilator as described above. The kit may include a device and a plurality of dilators, which may be reusable, or disposable. Where the dilators are disposable, replacement packs of disposable dilators could be supplied separately.

Preferred embodiments of the present invention are described below, by way of example only, with reference to the accompanying drawings, in which.

Figure 1:
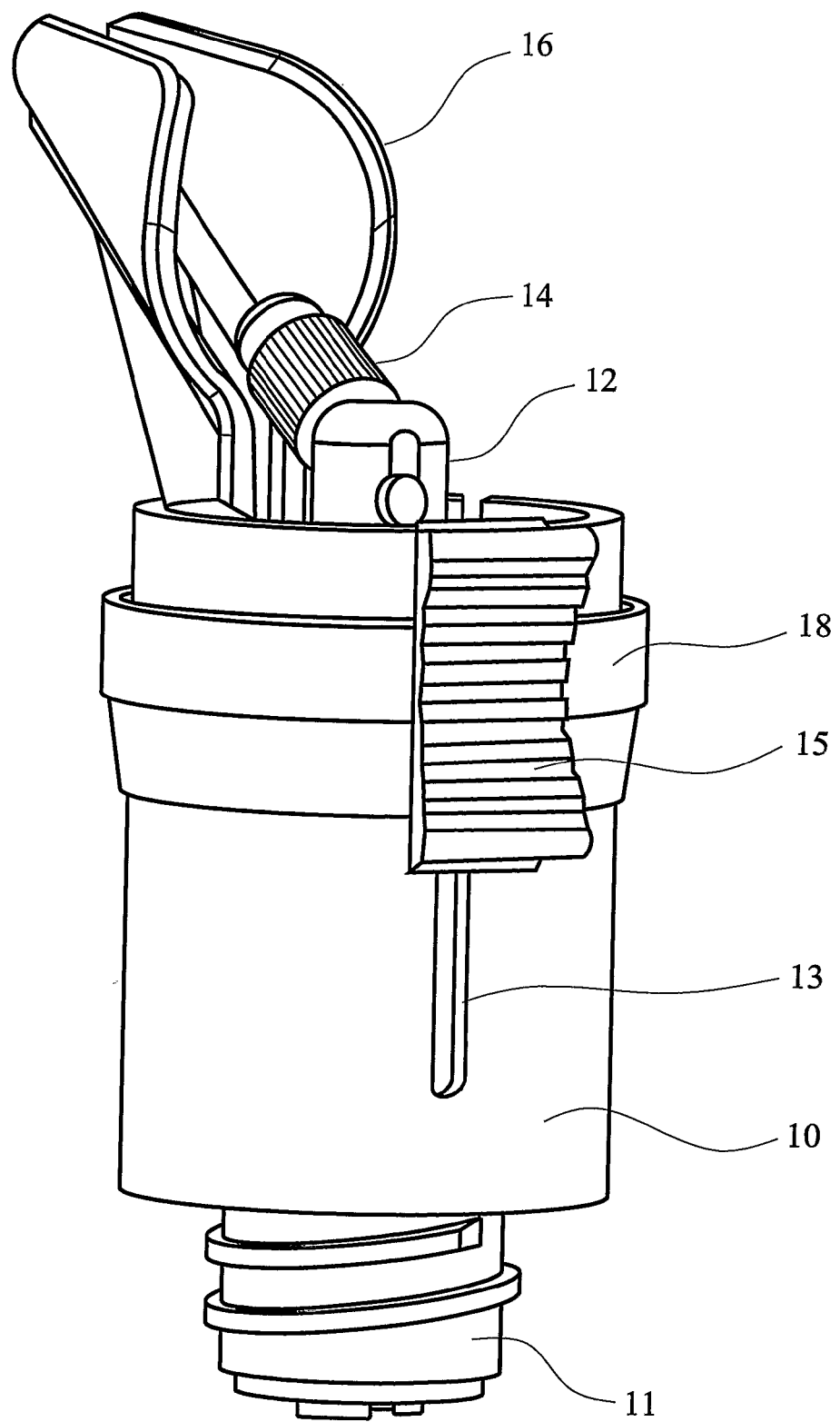
FIG. 1 is a perspective view of a device for facilitating examination of a nose, and an attached dilator, in accordance with a first embodiment of the invention.
Figure 2:
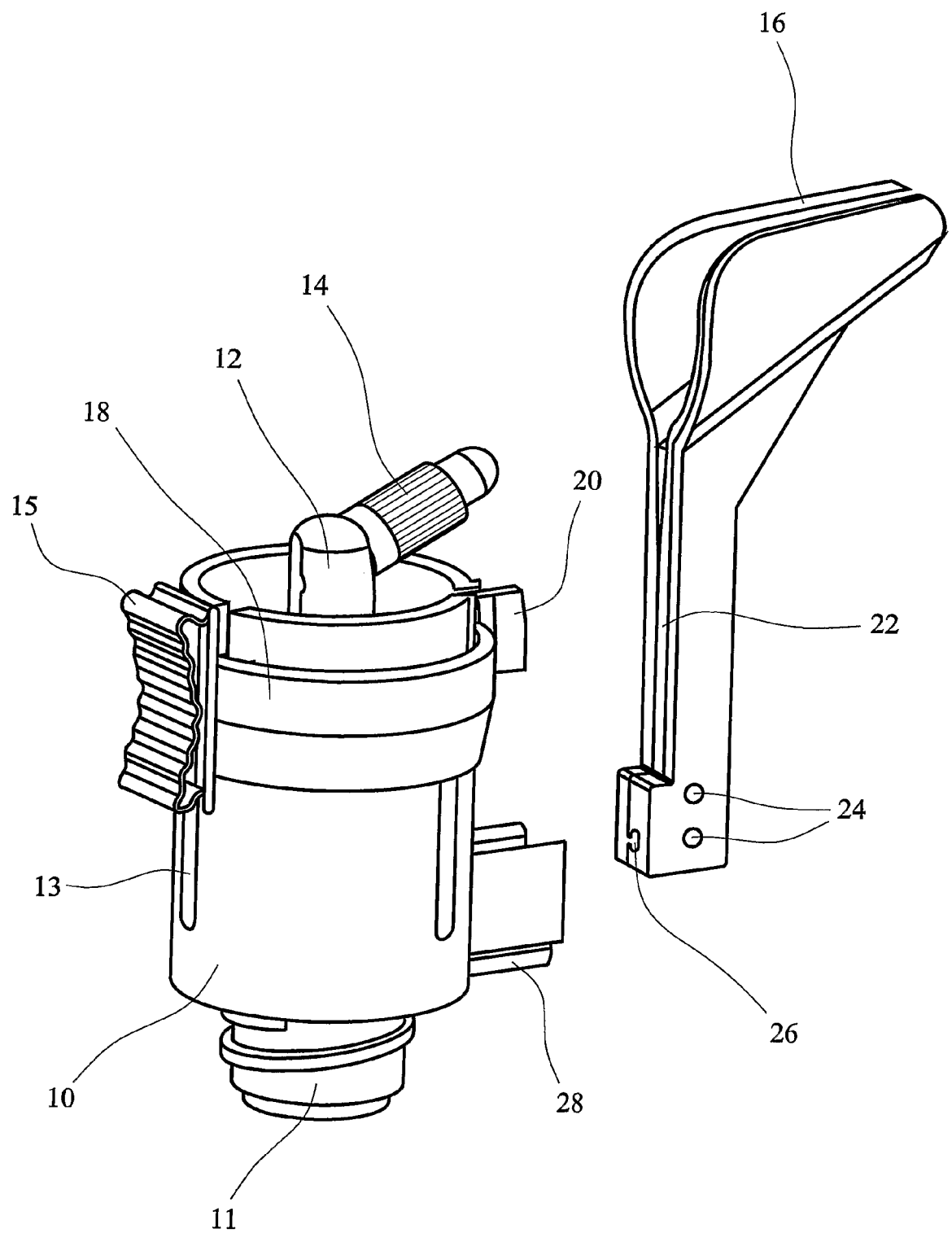
FIG. 2 is a first perspective view of the device and dilator of FIG. 1 in a detached configuration.

FIG. 1 illustrates a rhinoscope having an attached nasal speculum 16 in accordance with a first embodiment of the present invention. The rhinoscope includes an outer casing 10 having a threaded connection 11 for connection to a handheld battery unit (not shown in FIG. 1), which preferably provides power at 3 volts. A light bulb 14 is electrically connected to a central core 12 and is arranged to direct light towards the dilating part of a nasal speculum 16 (see below). The central core 12 contains appropriate electrical wiring and electrical connections to provide power from the battery unit to the light bulb 14. An outer ring 18 is mounted around the casing 10 and is slidably movable by about 2 cm along the longitudinal axis of casing 10. A thumb engagement member 15 is provided on a rear surface of the outer ring 18.

The nasal speculum 16 for use with this rhinoscope is disposable and detachably mounted to the casing 10. The speculum 16 is fabricated from a relatively rigid, but resiliently deformable, plastic material and is roughly the shape of an upside down "L". It has an upright section approximately 4 cm in length. At the upper end of this is a transverse section extending from the upright section at an angle of approximately 100-110°. The nasal speculum 16 comprises two separate blades that are connected at their lower ends by a tongue and groove feature 26 in order to form a single speculum. The upper, transversely extending, section is suitable for insertion into a nostril. The upper sections of the blades are not connected together. They can thus be separated by around 2-3 mm, in use, in order to dilate a nostril into which the speculum 16 has been inserted. When looking along the longitudinal axis of the upper section, it can be seen that the profiles of the outer surfaces of the speculum blades are rounded (convex). This reduces discomfort for the patient, and enables a doctor to look between the blades into the nostril. Moreover, the generally funnel-shaped construction of the dilator at its upper, operative end enables medication and vaccines (such as an AIDS vaccine) to be delivered through the nose.

The rear surface 22 of the upright section of the nasal speculum 16 that faces the casing 10 of the device, when the nasal speculum 16 is correctly mounted, includes a "V"-shaped groove between the two blades, such that the edges of the blade that define the groove converge towards their lower end.

The casing 10 is provided with a clip 28, which is designed to cooperate with, and engage, a lower portion of the nasal speculum 16. This is described in further detail with reference to FIG. 4 below. Two small depressions 24 are provided at the lower end of the nasal speculum 16 to aid engagement of the speculum 16 within the clip 28.

The outer ring 18 includes an actuating projection 20 mounted in a diametrically opposite position relative to the thumb engagement member 15. The actuating projection 20 can be inserted into an upper end of the "V"-shaped groove provided between the two blades of the nasal speculum 16.

Figure 3:
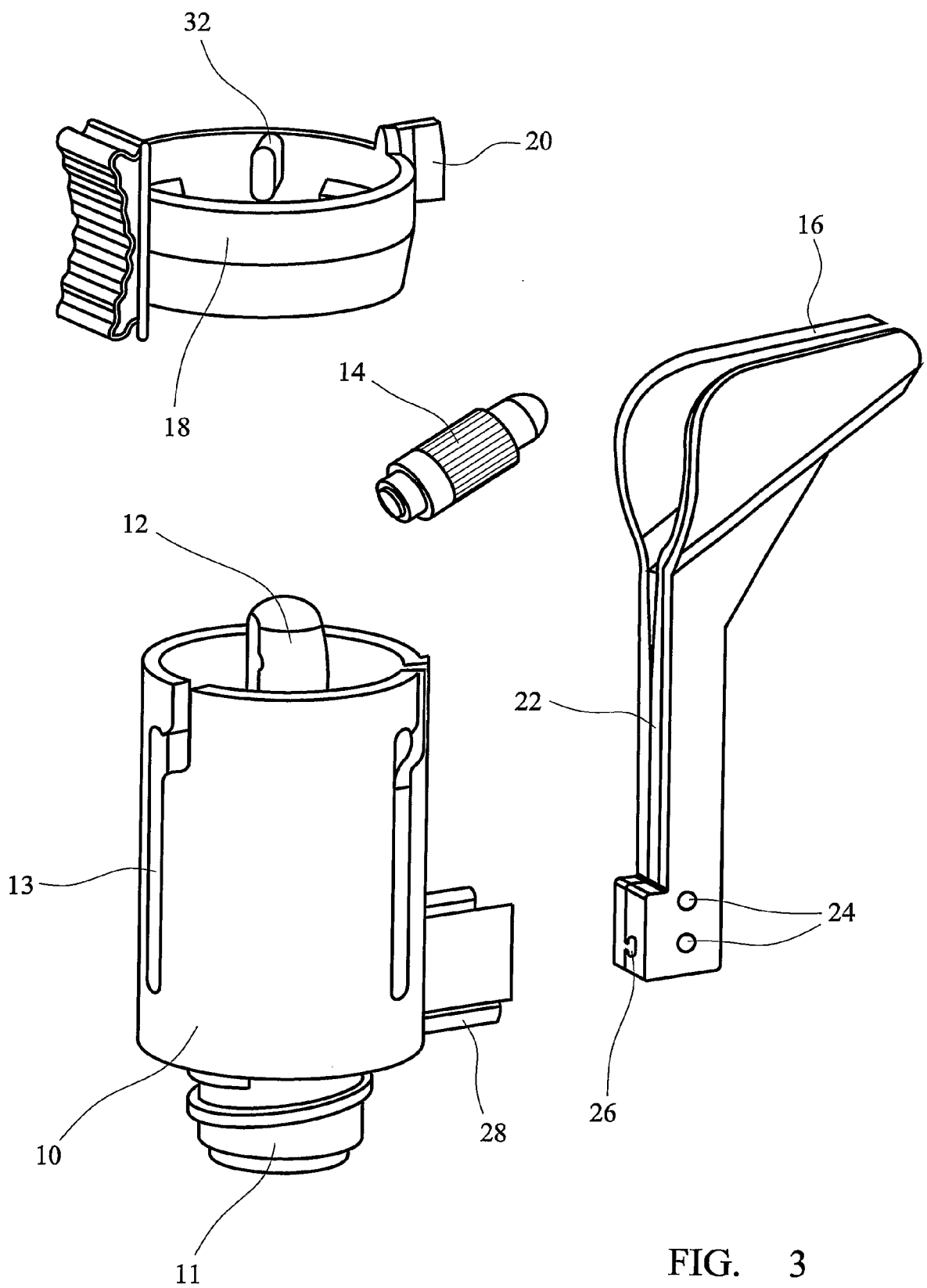
FIG. 3 is a partially exploded view of the device and dilator of FIG. 1.

As shown in FIG. 3, outer ring 18 is also provided with lugs 32 that project radially inwardly from the internal surface of outer ring 18. The lugs 32 engage within vertical slots 13 provided in the casing 10 in order to retain the outer ring 18 around the casing 10. A spring (not visible in the Figures) is provided within the casing 10 to bias the outer ring 18 towards the top of the casing 10. Preferably, each of the slots 13 includes a dogleg formation at its upper end so that the outer ring 18 can only be removed from the casing 10 if rotated by the user. This feature reduces the risk that the outer ring 18 is inadvertently removed from the casing 10.

Figure 4:
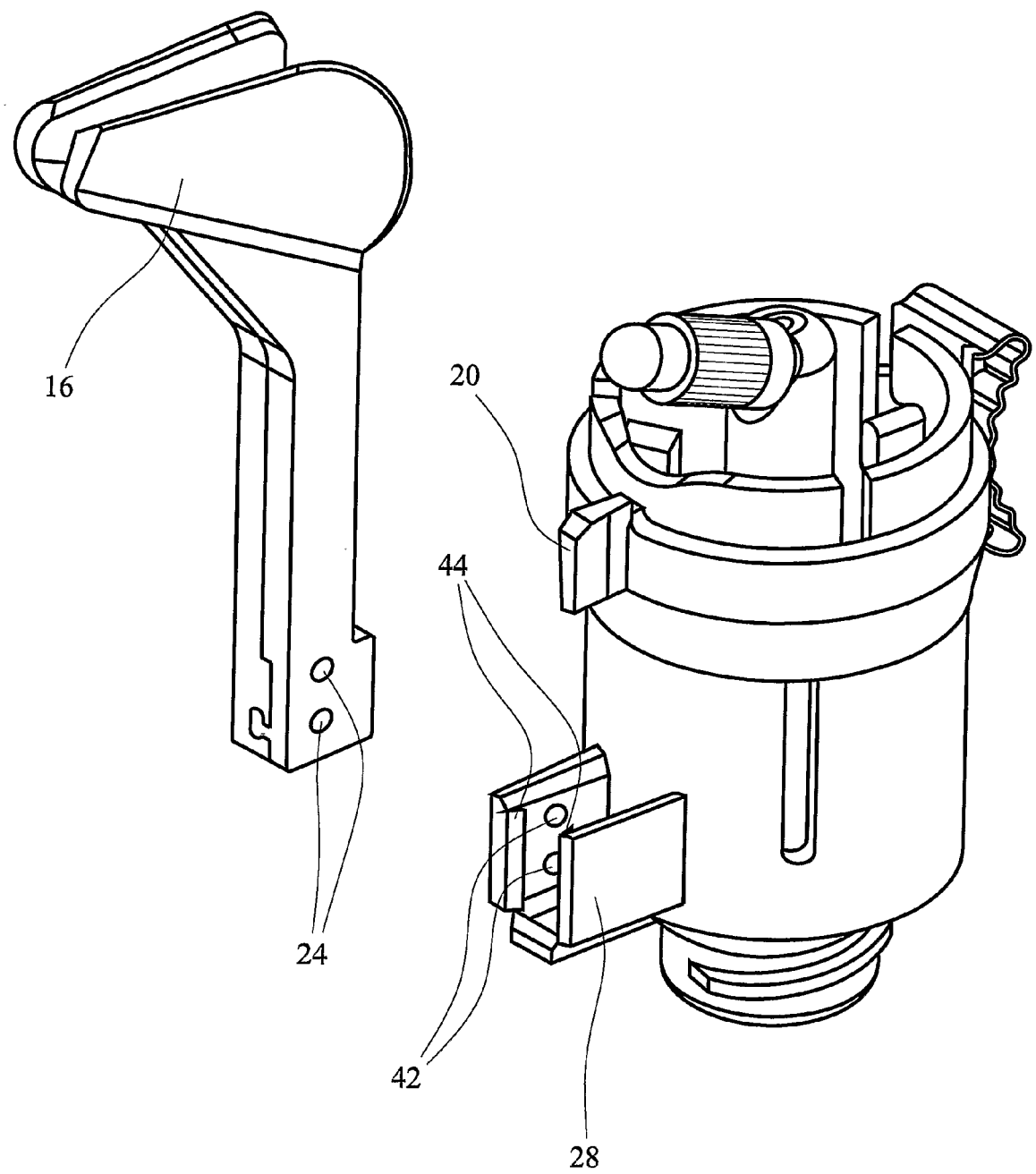
FIG. 4 is a second perspective view of the device and dilator of FIG. 1 in a detached configuration.

Referring now to FIG. 4, further detail of the clip 28 can be seen. The clip 28 comprises three walls: two lateral walls and an inferior wall located at the lower ends of the two lateral walls. The three walls together form a "U"-shape into which the lower portion of the speculum 16 can be located.

As indicated above, two depressions 24 are provided at the lower end of the speculum 16. Corresponding projections 42 are provided inside the clip 28 on the lateral walls. Location of the projections 42 within the corresponding depressions 24 helps to stabilise the speculum 16 when it is placed in the clip 28.

The outer edges of the lateral walls each include a resilient flange 44. The flanges 44 assist in retaining the nasal speculum 16 in place within the clip 28. In use, the casing 10 is screwed onto a handheld battery unit such that the bulb 14 is electrically connected to a battery. Switching on of the battery unit thus causes the bulb 14 to illuminate. A nasal speculum 16 can be clipped onto the casing 10 by means of the clip 28. This is done in such a way that the actuating projection 20 extends into an upper end of the "V" shaped groove provided between the blades of the nasal speculum 16.

In use, the doctor inserts the nasal speculum 16 gently into a nostril to be examined. With his thumb positioned on the thumb engagement member 15, the doctor is able to dilate the nostril. In particular, gentle downwards movement of the thumb engagement member 15 (and hence outer ring 18), against the bias of the spring, causes the actuating projection 20 to move downwards along the V-shaped groove between the blades of the nasal speculum 16. As the width of the grove reduces, the downwards movement of the actuating projection 20 causes the blades to move apart slightly, thereby causing the upper sections of the blades of the nasal speculum 16 to move apart, to dilate the nostril.

At the end of the examination, the doctor can simply detach the nasal speculum 16 from the casing 10 and dispose of it safely. Removal of the speculum 16 can be achieved by placing the index finger in between the two opposing parts at their upper ends thereby dilating the speculum 16 and freeing it from the actuating projection 20. By flexing the top end of the speculum 16 forward, it is released from the clipping actions of the walls of the clip 28 supporting its bottom end, thereby allowing its detachment. A new disposable nasal speculum 16 can be attached to the casing 10 prior to examination of a subsequent patient.

Figure 5:
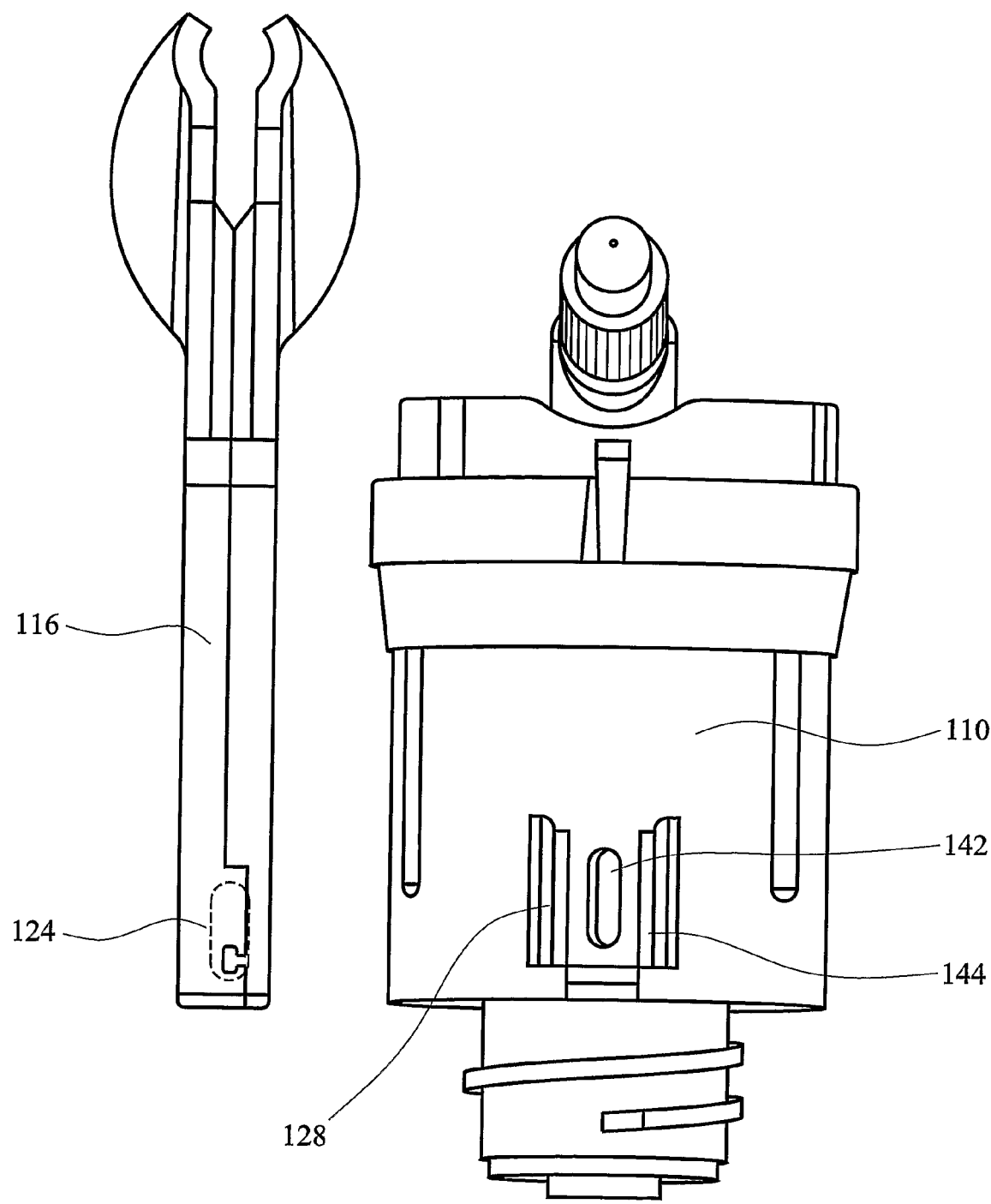
FIG. 5 is a perspective view, which shows hidden detail, of a device for facilitating examination of a nose, and an attached dilator, in accordance with a second embodiment of the invention.

FIG. 5 illustrates a rhinoscope and an associated speculum 116 in accordance with a second embodiment of the present invention. The rhinoscope and speculum 116 of the second embodiment differ from the corresponding components of the first embodiment in that the four depressions 24 on the lateral surfaces of the speculum 16 have been replaced by a single central depression 124 in a rear surface of the lower end of the speculum 116. Similarly, the four projections 42 on the interior lateral surfaces of the clip 28 have been replaced by a single central projection 142 in a front surface of the casing 110. The speculum 116 is attached to the clip 128 by sliding the lower end of the speculum 116 between the lateral walls of the clip 128 until the central projection 142 of the rhinoscope is located within the central depression 124 of the speculum 116, and the resilient flanges 144 extend at least partially across a front surface of the speculum 116. The flanges 144 assist in retaining the speculum 116 in place within the clip 128.

The arrangement shown in the embodiment of FIG. 5 has advantages in the connection and disconnection of the speculum 116, which is easier because the lower end of the speculum 116 need only be pushed into/pulled out of position.

Figure 6:
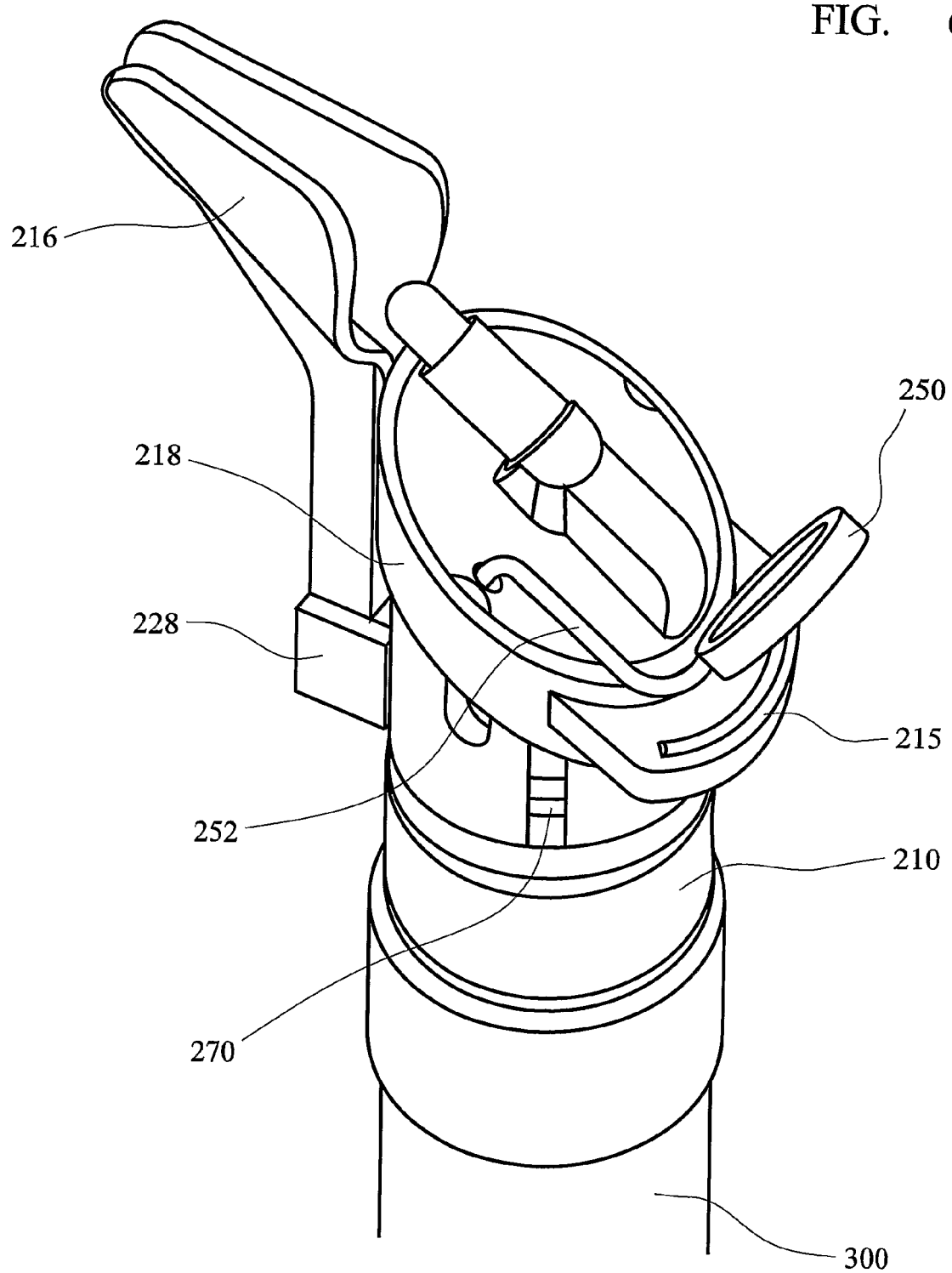
FIG. 6 is a perspective view, which shows hidden detail, of a device for facilitating examination of either a nose or an ear, and an attached dilator, in accordance with a third embodiment of the invention.
Figure 7:
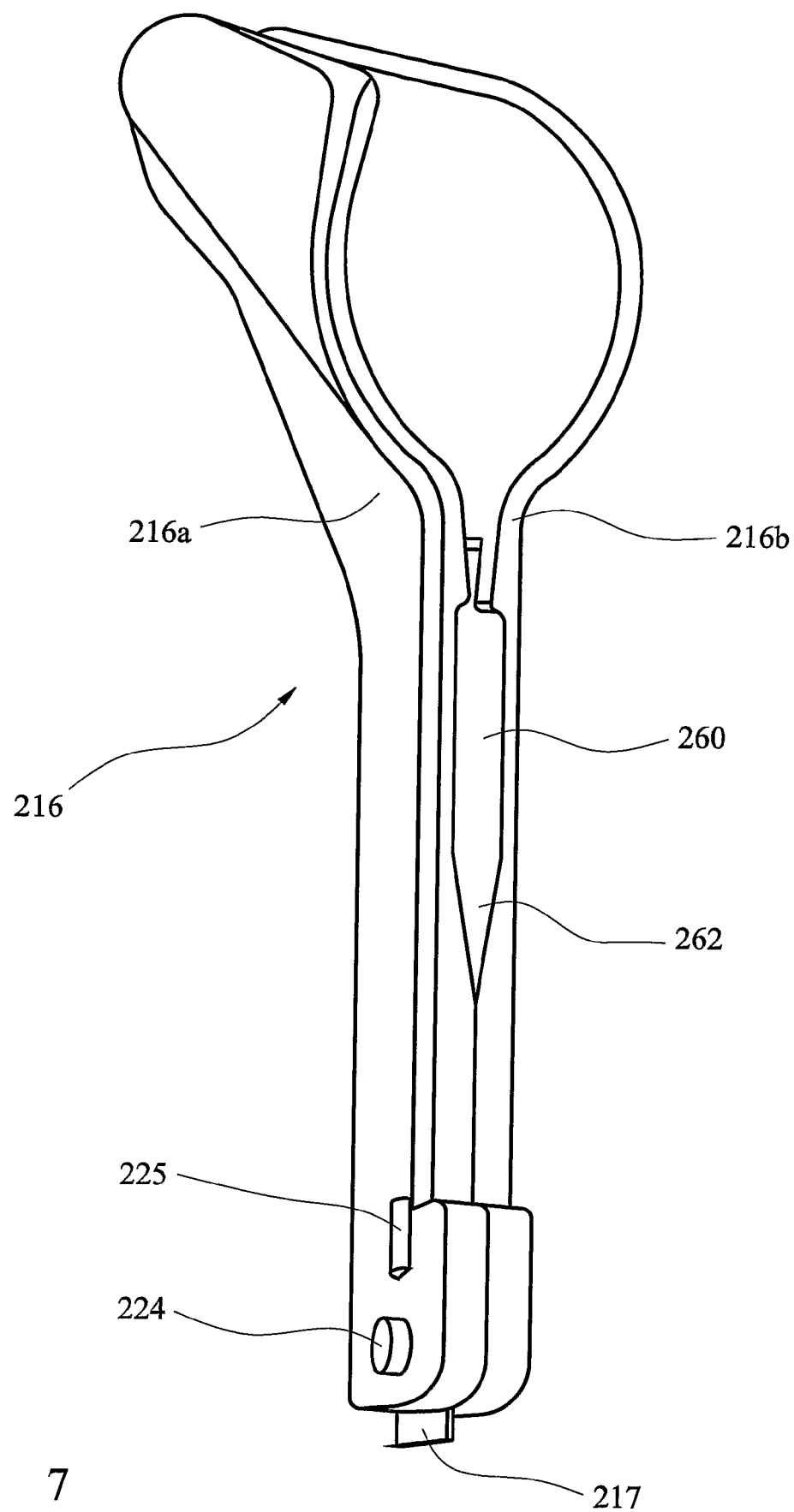
FIG. 7 is a perspective view of the dilator of FIG. 6.
Figure 8:
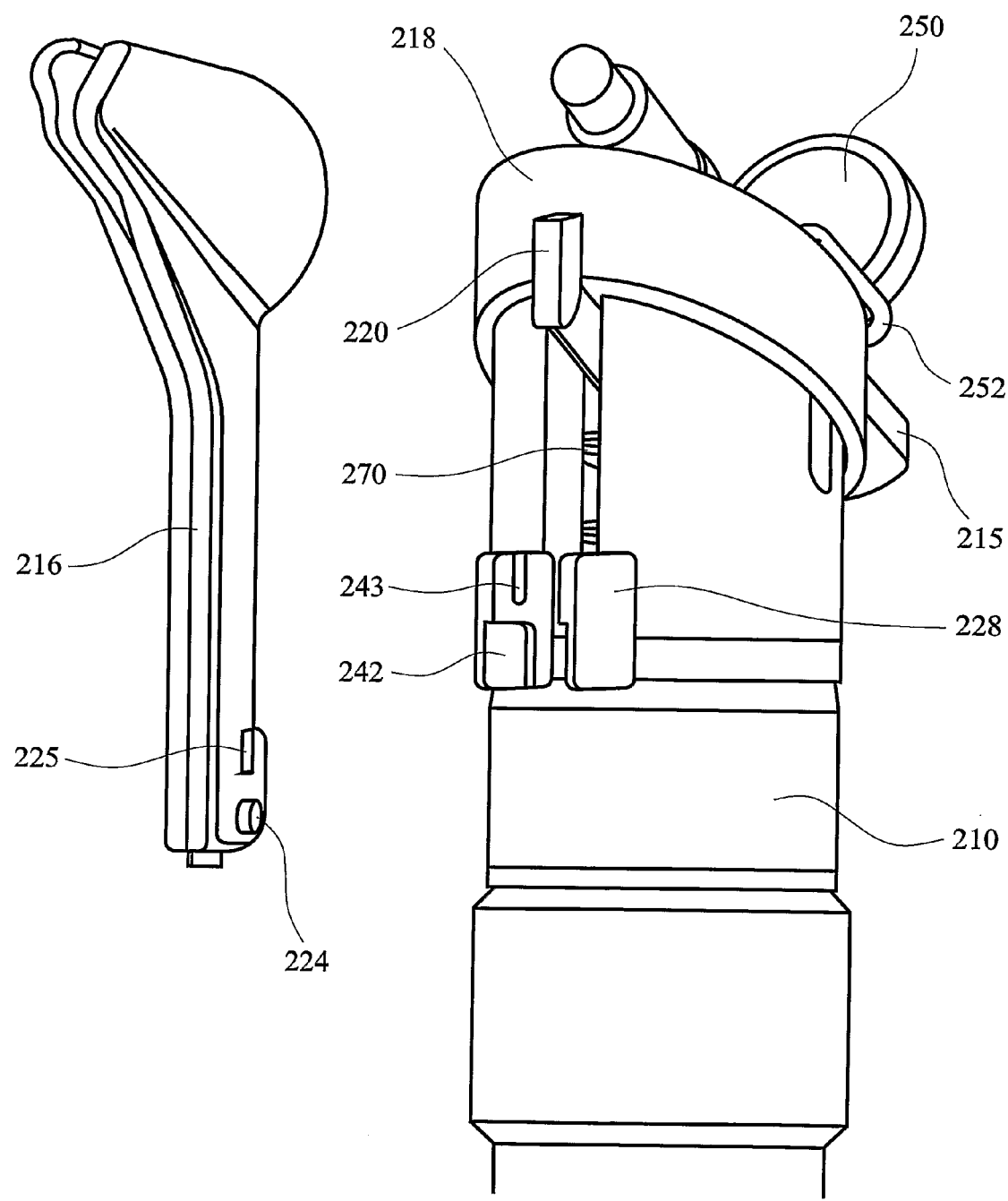
FIG. 8 is a perspective view of the device and associated dilator of FIG. 6 in a detached configuration.

FIGS. 6 to 8 illustrate a presently preferred device for facilitating examination of either the nose or an ear of a patient, and an associated speculum 216, in accordance with a third embodiment of the present invention. The device is shown with its casing 210 attached to the upper end of a conventional battery unit 300. This device is similar to the devices 10,110 of the first and second embodiments, but differs principally in that the device is suitable for examining either the nose or an ear of a patient, and the construction of the speculum 216, the clip 218 and the actuating member 215 have been modified.

The presently preferred device includes a magnifying lens 250 that is mounted to an upper surface of the device by an arm 252. The arm 252 is rotatably mounted to the upper surface of the device, about an axis that is perpendicular to the upper surface, so that the lens 250 is movable from an operative position in which the lens 250 enables a magnified view between the blades of the speculum 216 into the orifice being examined, to an inoperative position in which the lens 250 is entirely removed from the lines of sight into the orifice between the blades of the speculum 216. This feature enables the device to facilitate examination of the nose or an ear of a patient, and hence act as either a rhinoscope or an otoscope, as necessary.

The casing 210 and the outer ring 218 of the device are similar to the casings 10,110 and outer rings 18,118 of the first and second embodiments, save that the upper surfaces of the casing 210 and the outer ring 218 are orientated at an angle to the longitudinal axis of the device, such that a front end of the upper surface of the casing 210 and a front end of the outer ring 218 are raised (as viewed in FIG. 6) relative to their rear ends. Furthermore, the thumb engagement member 215 at the rear end of the outer ring 218 has the form of a platform upon which a user's thumb may rest, so that downward movement of the thumb causes the outer ring 218 to slide downwards, against the biasing of the spring 270, along the exterior surface of the casing 210. This thumb engagement member 215 includes a raised formation that acts as a grip, and is accessible from both sides of the device so as to facilitate operation by the right or left hand of a user.

The speculum 216 is shown from the rear in FIG. 7. The speculum 216 comprises first and second opposing blades 216a,216b that are connected by a hinge 217 at their lower ends. The speculum 216 is injection moulded as a unitary component including the first and second blades 216a,216b and the hinge 217, and then folded into the closed configuration shown in FIG. 7. Engagement of the lower end of the speculum 216 with the clip 228 of the device maintains the speculum 216 in its closed configuration, unless acted upon by the projection 220 of the outer ring 218, as described in more detail below in relation to FIG. 8.

Each blade 216a,216b of the speculum 216 has an upright section approximately 4 cm in length, and at the upper end of this upright section is a transverse section extending from the upright section at an angle of approximately 100-110°. The transverse sections of the blades together define a generally funnel-shaped member, in the closed configuration of the speculum 216, that has an opening that extends along its upper surface. Each of the blades 216a,216b has a recess formed in the rear surface of its upright section, such that the two recesses are adjacent to each another in the closed configuration of the speculum 216 and together define a groove that extends along a central, longitudinal axis of the rear surface of the speculum 216. The groove 216 of the speculum has an upper section 260 and a lower section 262.

The upper end of the upper section 260 is adapted to receive the projection 220 in the closed configuration of the speculum 216, with a relatively close fit, such that the lateral surfaces of the projection 220 are in contact with the adjacent surfaces of the blades 216a,216b. The upper section 260 of the groove reduces in width gradually until it reaches the lower section. As the projection 220 is moved, in use, down the upper section 260 of the groove, towards the lower section 262, the projection 220 will urge the surfaces of the blades 216a,216b with which it is in contact gradually outwards relative to each other. Since the blades 216a,216b are connected at their lower end, and unconnected at their upper end, this will cause the blades 216a,216b to gradually increase in separation at their upper end. This gradual increase in the separation of the blades 216a,216b at their upper end, which is caused by movement of the projection 220 along the upper section 260 of the groove, is suitable for accurate dilation of an orifice by a small amount, and hence is particularly suitable for dilation of an ear.

The lower section 262 of the groove reduces in width more rapidly than the upper section 260, as shown clearly in FIG. 7, until the adjacent surfaces of the blades 216a,216b contact each other at a lower end of the groove. As the projection 220 is moved, in use, down the lower section 262 of the groove, towards its lower end, the projection 220 will urge the surfaces of the blades 216a,216b with which it is in contact outwards relative to each other, at an increased rate relative to movement of the actuating member than when the projection 220 moves along the upper section 260. Since the blades 216a,216b are connected at their lower end, and unconnected at their upper end, this will cause the blades 216a,216b to increase in separation at their upper end, also at an increased rate relative to movement of the actuating member than when the projection 220 moves along the upper section 260. This more rapid increase in the separation of the blades 216a,216b at their upper end, which is caused by movement of the projection 220 along the lower section 262 of the groove, is suitable for greater dilation of an orifice, and hence is particularly suitable for dilation of a nose.

Referring now also to FIG. 8, the lower end of the speculum 216 includes a generally cylindrical projection 224 on each of its lateral surfaces, and a rib projection 225 above each of the cylindrical projections 224. The clip 228 to which the lower end of the speculum 216 is connected has lateral walls only, between which the lower end of the speculum 216 is received. The interior surfaces of the lateral walls include opposed square-shaped depressions 242, which are open at their front and underside ends and adapted to receive the cylindrical projections 224 of the speculum 216, and opposed grooves 243 adapted to receive the rib projections 225 of the speculum 216. This arrangement enables the lower end of the speculum 216 to be slid into engagement with the clip 228, with the cylindrical projections located within the square-shaped depressions 242, until the rib projections 225 of the speculum 216 locate within the grooves 243 of the clip 228. Disengagement of the speculum 216 from the device may be achieved by urging the upper end of the speculum 216 away from the device, such that the rib projections 225 of the speculum 216 are removed from the grooves 243 of the clip 228, and the lower end of the speculum 216 may then be slid out of engagement with the clip 228. The cylindrical projections 224 of the speculum 216 act as a fulcrum of a lever as the upper end of the speculum 216 is urged away from the device, and hence removal of the rib projections 225 of the speculum 216 from the groove depressions 243 of the clip 228 is facilitated.

The skilled person would appreciate that many of the features of the preferred embodiments are described by way of example only, and that there are many modifications that could be made whilst still obtaining the advantages conferred by the present invention.

The invention claimed is:

1. An apparatus for facilitating the examination of an orifice of a nose or ear, the apparatus comprising:
    a device having
        a mount for a light source for illuminating the orifice,
        a dilator connector, and
        a dilator actuator for operating a dilator, said dilator actuator being part of the device and comprising a moveable actuating projection, wherein the moveable actuating projection is moveable relative to the dilator connector;
    the apparatus further comprising:
        said dilator;
        wherein said dilator is for insertion into and dilation of an orifice in use, said dilator having a first portion that is detachably mountable to said dilator connector such that said dilator is detachable therefrom, said dilator including operative parts able to move apart from one another and a groove of gradually reducing width,
    wherein the dilator connector and the dilator actuator are configured such that when the first portion of the dilator is mounted to said dilator connector said actuating projection of the dilator actuator engages the dilator at a location that is remote from said first portion and the actuating projection is moveable within said groove of said dilator so as to urge the operative parts of the dilator apart from one another.

2. An apparatus as claimed in claim 1, wherein the device comprises a casing and the dilator connector is adapted to fasten parts of the dilator to the device in a fixed position relative to said casing of the device.

3. An apparatus as claimed in claim 1, wherein the actuating projection is movable by a user, either directly or by means of an operably connected engagement member, to actuate the dilator.

4. An apparatus as claimed in claim 3, wherein the actuating projection is biased to an inoperative configuration, in which the dilator has a contracted configuration.

5. An apparatus as claimed in claim 3, wherein the actuating projection or the operably connected engagement member is adapted to be moved by the thumb or a finger of a user.

6. An apparatus as claimed in claim 5, wherein the actuating projection or the operably connected engagement member includes a platform with an operative surface upon which a user's thumb or finger may rest, and pressure applied by a user's thumb or finger to the operative surface causes movement of the actuating projection.

7. An apparatus as claimed in claim 1, wherein the actuating projection is slidably mounted to the exterior of a casing of the device.

8. An apparatus as claimed in claim 1, wherein the device is suitable for facilitating examination of a nostril, and the device is also suitable for facilitating examination of an ear.

9. An apparatus as claimed in claim 8, wherein the device includes a magnifying lens that is able to provide an enlarged view of the interior of an ear.

10. An apparatus as claimed in claim 9, wherein the magnifying lens is movably mounted to the device.

11. An apparatus as claimed in claim 10, wherein the lens is movable between an operative position in which it is able to provide an enlarged view of the interior of the orifice, and an inoperative position in which the view of the orifice, in use, through the dilator is unobstructed by the lens.

12. An apparatus as claimed in claim 11, wherein the lens is mounted to a rotatable arm, such that rotation of the arm causes the lens to be moved between operative and inoperative positions.

13. An apparatus as claimed in claim 12, wherein the arm is mounted to an upper surface of the device, the arm being rotatable about an axis that is laterally offset from the lines of sight through the dilator, and is orientated generally perpendicularly to the upper surface of the device.

14. An apparatus as claimed in claim 1, wherein the dilator connector for detachably mounting the dilator includes formations that engage with corresponding formations of the dilator, so as to fasten the dilator to the device.

15. An apparatus as claimed in claim 1, wherein the mount for a light source is a connector adapted for electrically connecting the device to a mounted light source.

16. An apparatus as claimed in claim 15, wherein the device includes a further connector adapted for connection to a power source for the supply of power to said mounted light source.

17. An apparatus as claimed in claim 16, wherein the device includes a threaded connection that enables the device to be connected to existing battery units used for other diagnostic devices.

18. A kit comprising the apparatus of claim 1, wherein the kit includes a plurality of said dilators, which may be reusable, or disposable.

19. A dilator for use with a device for facilitating the examination of an orifice of an ear or nose, the dilator being configured for insertion into and dilation of the orifice and comprising:
    a L-shaped body having an upright section and a transverse section extending at a non-zero angle from the upright section, the L-shaped body comprising opposing blades for insertion into an orifice in use,
    wherein the transverse section comprises transverse sections of the opposing blades;
    wherein the upright section comprises:
        a first portion configured to be detachably mounted to a connector of the device, said first portion comprising a single connector at a terminal end of the L-shaped body being common to the opposing blades, the single connector connecting the opposing blades to each other at terminal ends of the opposing blades;
        a second portion remote from the first portion, said second portion comprising portions of each blade having a recess formed in a rear surface of the blades, wherein the two recesses are adjacent to each other in a closed configuration of the dilator and together define a groove of gradually reducing width in a direction towards the first portion, said portions of each blade having the recess being adapted to be urged apart by movement of an actuating projection of the device relative to the dilator within said groove of gradually reducing width, such that said sections of each blade having the recess move apart from one another and thereby urge apart the transverse sections of the opposing blades to permit viewing of an interior of the orifice, and
        a third portion, between the first portion and the second portion, wherein, in the closed configuration of the dilator, the third portion comprises portions of the opposing blades in contact with each other along the entire length of the third portion, wherein the third portion does not have a groove between the blades; wherein the opposing blades are sufficiently resilient such that the opposing blades are configured to return to the closed configuration when not actuated by the device.

20. A dilator as claimed in claim 19, wherein the single connector includes formations adapted to cooperate with corresponding formations of the connector of the device.

21. A dilator as claimed in claim 19, wherein the transverse sections of the opposing blades together define a generally funnel-shaped member.

22. A dilator as claimed in claim 21, wherein the transverse sections of the opposing blades have a separation at all times, in use.

23. A dilator as claimed in claim 19, wherein the upright section of the L-shaped body includes a weakened portion that reduces the force required to separate the transverse sections of the opposing blades.

24. A dilator as claimed in claim 19, wherein an end of the groove adjacent to the transverse sections of the opposing blades is able to accommodate the actuating projection of the device when the dilator is in the closed configuration, and subsequent movement of the actuating projection along the groove towards the single connector causes a smooth and gradual separation of the transverse sections of the opposing blades.

25. A dilator as claimed in claim 19, wherein the groove between the opposing blades includes two or more sections that reduce in width at different rates, and hence cause different rates of separation of the transverse sections of the opposing blades relative to movement of the actuating projection along the groove.

26. A dilator as claimed in claim 25, wherein the groove includes a first section that causes separation of the transverse sections of the opposing blades at a first rate relative to movement of the actuating projection along the groove, and a second section that causes separation of the transverse sections of the opposing blades at a second rate relative to movement of the actuating projection along the groove, the second rate of separation being greater than the first rate.

27. A dilator as claimed in claim 26, wherein the first section is formed at the end of the groove adjacent to the transverse sections of the opposing blades, and the second section is formed at an end of the groove adjacent to the third portion of the opposing blades.

28. A dilator as claimed in claim 27, wherein separations of the transverse sections of the opposing blades caused by the first section of the groove are suitable for dilation of an ear, and separations of the transverse sections of the opposing blades caused by the second section of the groove are suitable for dilation of a nose.

29. A dilator as claimed in claim 19, wherein the opposing blades are separately formed.

30. A dilator as claimed in claim 19, wherein the upright section comprises upright sections of the opposing blades, and the upright section and the transverse section of one of the opposing blades are integrally formed.

31. A dilator as claimed in claim 19, wherein the opposing blades are a unitary component.

32. A device for facilitating examination of an orifice of an ear or nose, the device comprising:
a mount for a light source for illuminating the orifice,
a dilator connector for detachably mounting a dilator for insertion into and dilation of an orifice, and
a dilator actuator for operating a mounted dilator, said dilator actuator being part of the device such that the dilator is detachable therefrom, wherein the dilator actuator comprises an actuating projection at a location on the device which is remote from the dilator connector, the actuating projection being moveable relative to the dilator connector in a linear direction towards the dilator connector such that the actuating projection is engageable with the mounted dilator at a location spaced from the dilator connector and moveable within a groove of gradually reducing width of the dilator to urge operative parts of the dilator apart from one another such that the dilator can dilate an orifice into which it is inserted so as to permit examination of the orifice in use.

33. A device according to claim 32, wherein the device comprises a casing and the dilator actuator is slidably mounted relative to the casing.

34. A device according to claim 32, wherein the device comprises a casing having one or more slots therein and the dilator actuator is engaged with said one or more slots.

* * * * *